(12) United States Patent
Messner et al.

(10) Patent No.: US 9,763,775 B2
(45) Date of Patent: Sep. 19, 2017

(54) INTRAOCULAR LENS STORAGE SYSTEM

(71) Applicant: HumanOptics AG, Erlangen (DE)

(72) Inventors: Arthur Messner, Schnaittach (DE); Martin Christoph Heiss, Eggerstanden (CH)

(73) Assignee: HumanOptics AG, Erlangen (DE)

( * ) Notice: Subject to any disclaimer, the term of this patent is extended or adjusted under 35 U.S.C. 154(b) by 185 days.

(21) Appl. No.: 14/653,951

(22) PCT Filed: Dec. 13, 2013

(86) PCT No.: PCT/EP2013/076504
§ 371 (c)(1),
(2) Date: Jun. 19, 2015

(87) PCT Pub. No.: WO2014/095611
PCT Pub. Date: Jun. 26, 2014

(65) Prior Publication Data
US 2015/0342730 A1     Dec. 3, 2015

(30) Foreign Application Priority Data
Dec. 20, 2012    (DE) .......................... 10 2012 223 885

(51) Int. Cl.
*A61F 2/16*     (2006.01)

(52) U.S. Cl.
CPC ............ *A61F 2/1691* (2013.01); *A61F 2/167* (2013.01); *A61F 2/1678* (2013.01)

(58) Field of Classification Search
CPC .... A45C 11/005; A61F 2/1662; A61F 2/1667; A61F 2/167; A61F 2/1672; A61F 2/1675; A61F 2/1678; A61F 2/1691
See application file for complete search history.

(56) References Cited

U.S. PATENT DOCUMENTS

| 4,173,281 | A | * | 11/1979 | Trought | ................ | A61F 2/1691 |
| | | | | | | 206/210 |
| 4,257,521 | A | * | 3/1981 | Poler | ..................... | A61F 2/1691 |
| | | | | | | 206/205 |
| 4,423,809 | A | * | 1/1984 | Mazzocco | ................. | A61F 2/16 |
| | | | | | | 206/210 |

(Continued)

FOREIGN PATENT DOCUMENTS

| CN | 1118247 A | 3/1996 |
| DE | 10 2006 000929 A1 | 7/2007 |

(Continued)

OTHER PUBLICATIONS

Chinese Office Action of Dec. 28, 2015.

*Primary Examiner* — Ryan J Severson
(74) *Attorney, Agent, or Firm* — McGlew and Tuttle, P.C.

(57) ABSTRACT

An intraocular lens storage system for storing an intraocular lens. The intraocular lens storage system includes a storage container for storing the intraocular lens and an actuable transfer device, which is arranged in the storage container, with an intraocular lens receiver to receive the intraocular lens. The transfer device is movable between an intraocular lens storage position for storing the intraocular lens in the storage container and an intraocular lens transfer position to transfer the intraocular lens to an injection device.

12 Claims, 9 Drawing Sheets

(56) References Cited

U.S. PATENT DOCUMENTS

| | | | | |
|---|---|---|---|---|
| 4,697,697 A * | 10/1987 | Graham | A61F 2/1691 | 206/205 |
| 4,862,885 A * | 9/1989 | Cumming | A61F 2/1664 | 606/107 |
| 5,019,084 A * | 5/1991 | Aysta | A01N 1/02 | 206/5.1 |
| 5,171,241 A * | 12/1992 | Buboltz | A61F 2/1691 | 606/1 |
| 5,578,042 A * | 11/1996 | Cumming | A61F 2/1662 | 128/898 |
| 6,183,513 B1 * | 2/2001 | Guenthner | A61F 2/1691 | 206/316.1 |
| 6,228,094 B1 | 5/2001 | Erdman | | |
| 6,360,883 B1 * | 3/2002 | Haq | A45C 11/005 | 206/205 |
| 6,386,357 B1 * | 5/2002 | Egawa | A61F 2/1664 | 206/5.1 |
| 6,468,282 B2 * | 10/2002 | Kikuchi | A61F 2/1664 | 606/107 |
| 6,471,708 B2 * | 10/2002 | Green | A61F 2/1691 | 606/107 |
| 6,537,283 B2 * | 3/2003 | Van Noy | A61F 2/1691 | 414/416.04 |
| 6,733,507 B2 * | 5/2004 | McNicholas | A61F 2/1678 | 606/107 |
| 7,281,699 B2 * | 10/2007 | Hovey | A45C 11/005 | 206/438 |
| 7,422,604 B2 * | 9/2008 | Vaquero | A61F 2/167 | 623/6.12 |
| 7,429,263 B2 * | 9/2008 | Vaquero | A61F 2/1691 | 606/107 |
| 7,458,976 B2 * | 12/2008 | Peterson | A61F 2/1691 | 606/107 |
| 7,867,240 B2 * | 1/2011 | Peterson | A61F 2/1691 | 606/107 |
| 7,901,414 B2 * | 3/2011 | Tourrette | A61F 2/1678 | 606/107 |
| 7,988,701 B2 * | 8/2011 | Vaquero | A61F 2/1691 | 606/107 |
| 8,048,085 B2 * | 11/2011 | Peterson | A61F 2/1678 | 606/107 |
| 8,403,941 B2 * | 3/2013 | Peterson | A61F 2/1691 | 606/107 |
| 8,435,288 B2 * | 5/2013 | Isaacs | A61F 2/1664 | 623/6.12 |
| 8,470,030 B2 * | 6/2013 | Meunier | A61F 2/1678 | 606/107 |
| 8,475,526 B2 * | 7/2013 | Pynson | A61F 2/1664 | 623/6.12 |
| 8,475,527 B2 * | 7/2013 | Peterson | A61F 2/1678 | 623/6.12 |
| 8,506,575 B2 * | 8/2013 | Peterson | A61F 2/1678 | 606/107 |
| 8,523,877 B2 * | 9/2013 | Ichinohe | A61F 2/1662 | 606/107 |
| 8,562,674 B2 * | 10/2013 | Cole | A61F 2/1662 | 607/107 |
| 8,597,351 B2 | 12/2013 | Rathert | | |
| 8,603,163 B2 * | 12/2013 | Pynson | A61F 2/1664 | 623/6.12 |
| D707,821 S * | 6/2014 | Doraiswamy | D24/128 | |
| 9,277,989 B2 * | 3/2016 | Vaquero | A61F 2/1678 | |
| 9,339,374 B2 * | 5/2016 | Cole | A61F 2/1662 | |
| 9,364,320 B2 * | 6/2016 | Ichinohe | A61F 2/1662 | |
| 2002/0077633 A1 * | 6/2002 | Kikuchi | A61F 2/1664 | 606/107 |
| 2003/0036765 A1 * | 2/2003 | Van Noy | A61F 2/1691 | 606/107 |
| 2003/0045930 A1 * | 3/2003 | Nguyen | A61F 2/0095 | 623/5.11 |
| 2003/0195522 A1 * | 10/2003 | McNicholas | A61F 2/1678 | 606/107 |
| 2004/0199174 A1 * | 10/2004 | Herberger | A61F 2/1678 | 606/107 |
| 2004/0238392 A1 * | 12/2004 | Peterson | A61F 2/1678 | 206/438 |
| 2005/0049605 A1 * | 3/2005 | Vaquero | A61F 2/1691 | 606/107 |
| 2005/0049606 A1 * | 3/2005 | Vaquero | A61F 2/167 | 606/107 |
| 2005/0125000 A1 * | 6/2005 | Tourrette | A61F 2/1678 | 606/107 |
| 2005/0222579 A1 * | 10/2005 | Vaquero | A61F 2/1691 | 606/107 |
| 2006/0036262 A1 * | 2/2006 | Hohl | A61F 2/1691 | 606/107 |
| 2006/0142780 A1 * | 6/2006 | Pynson | A61F 2/1662 | 606/107 |
| 2006/0142781 A1 * | 6/2006 | Pynson | A61F 2/1691 | 606/107 |
| 2006/0184181 A1 * | 8/2006 | Cole | A61F 2/1662 | 606/107 |
| 2006/0200167 A1 * | 9/2006 | Peterson | A61F 2/1678 | 606/107 |
| 2007/0000801 A1 * | 1/2007 | Mauran | A61F 2/1664 | 206/438 |
| 2007/0055370 A1 | 3/2007 | Sorochkin et al. | | |
| 2007/0095700 A1 * | 5/2007 | Peterson | A61F 2/1678 | 206/438 |
| 2007/0123980 A1 * | 5/2007 | Peterson | A61F 2/1678 | 623/6.12 |
| 2007/0150055 A1 * | 6/2007 | Pynson | A61F 2/1664 | 623/6.12 |
| 2008/0058830 A1 * | 3/2008 | Cole | A61F 2/1664 | 606/107 |
| 2008/0077237 A1 * | 3/2008 | Isaacs | A61F 2/1664 | 623/6.12 |
| 2008/0119865 A1 | 5/2008 | Meunier et al. | | |
| 2008/0147080 A1 * | 6/2008 | Pynson | A61F 2/1691 | 606/107 |
| 2008/0154361 A1 * | 6/2008 | Pynson | A61F 2/1664 | 623/6.12 |
| 2009/0057167 A1 * | 3/2009 | Rathert | A61F 2/1691 | 206/205 |
| 2009/0062811 A1 * | 3/2009 | Peterson | A61F 2/1691 | 606/107 |
| 2009/0125034 A1 | 5/2009 | Pynson | | |
| 2009/0204122 A1 * | 8/2009 | Ichinohe | A61F 2/1662 | 606/107 |
| 2010/0280521 A1 * | 11/2010 | Vaquero | A61F 2/1691 | 606/107 |
| 2011/0046635 A1 | 2/2011 | Pankin et al. | | |
| 2011/0098716 A1 * | 4/2011 | Peterson | A61F 2/1678 | 606/107 |
| 2012/0016375 A1 * | 1/2012 | Peterson | A61F 2/1678 | 606/107 |
| 2014/0081284 A1 * | 3/2014 | Ichinohe | A61F 2/1662 | 606/107 |
| 2015/0342730 A1 * | 12/2015 | Messner | A61F 2/167 | 606/107 |

FOREIGN PATENT DOCUMENTS

| | | |
|---|---|---|
| EP | 2 286 762 A1 | 2/2011 |
| EP | 2 286 764 A1 | 2/2011 |
| FR | 2 875 125 A1 | 3/2006 |
| RU | 2 059 416 C1 | 5/1996 |
| RU | 36 216 U1 | 3/2004 |
| WO | 2006/070219 A1 | 7/2006 |

* cited by examiner

INTRAOCULAR LENS STORAGE SYSTEM

CROSS REFERENCE TO RELATED APPLICATIONS

This application is a United States National Phase application of International Application PCT/EP2013/076504 filed on Dec. 13, 2013 and claims the benefit of priority under 35 U.S.C. §119 of German patent application DE 10 2012 223 885.9 filed on Dec. 20, 2012, the entire contents of which are incorporated herein by reference.

FIELD OF THE INVENTION

The invention relates to an intraocular lens storage system for storing an intraocular lens. Furthermore, the invention is directed at an intraocular lens transfer arrangement for transferring an intraocular lens to an injection device with a corresponding intraocular lens storage system. The invention also relates to a method for transferring an intraocular lens to an injection device while providing a corresponding intraocular lens storage system.

BACKGROUND OF THE INVENTION

Intraocular lenses, which are artificial lenses for eyes, are stored in a sterile state until their use or implantation. It is known to use so-called primary packagings for this, which are in turn located in a secondary packaging, such as a sterile bag. Fixed or loose intraocular lens receivers to receive the intraocular lenses may be arranged in the primary packagings.

It is furthermore known to configure the primary packaging itself or the intraocular lens receiver as part of an injection device or as a complete injection device, so the intraocular lens can be implanted without manipulation, for example with tweezers, directly by means of the injection device.

The drawback in these known intraocular lens storage systems is that biocompatibility problems often occur. These are above all attributable to the use of slip additives, which can come into contact with the intraocular lenses while they are being sterilized and/or stored. The slip additives are generally contained in the materials used, which have slip properties.

SUMMARY OF THE INVENTION

Therefore, an object of the invention is to provide an intraocular lens storage system, in which biocompatibility problems can be substantially ruled out. Furthermore, an intraocular lens transfer arrangement is to be provided, in which biocompatibility problems can be substantially ruled out. A corresponding intraocular lens transfer method is also to be provided, in which biocompatibility problems can be substantially ruled out.

This object is achieved according to the invention by an intraocular lens storage system for storing an intraocular lens, comprising a storage container for storing the intraocular lens, and an actuable transfer device, which is arranged in the storage container, with an intraocular lens receiver for receiving the intraocular lens, wherein the transfer device is movable between an intraocular lens storage position for storing the intraocular lens in the storage container, and an intraocular lens transfer position for transferring the intraocular lens to an injection device, by an intraocular lens transfer arrangement with an intraocular lens storage system according to the invention, and with an injection device for introduction into the storage container of the intraocular lens storage system, wherein the transfer device in the intraocular lens transfer position transfers the intraocular lens to the injection device for implantation, and by a method for transferring an intraocular lens to an injection device, comprising providing an intraocular lens storage system according to the invention, and actuating the transfer device to move it from the intraocular lens storage position into the intraocular lens transfer position to transfer the intraocular lens to the injection device. The core of the invention is that the intraocular lens to be implanted is firstly arranged outside the injection device and, for example, at the planned implantation, is transferred or moved directly from the storage container to the injection device by means of the actuable transfer device. The intraocular lens can be transferred or moved directly from the storage container to the injection device by means of the actuable transfer device. The intraocular lens can be stored in a safe and sterile manner in the storage container.

It is advantageous if the intraocular lens storage system is produced from at least one thermoplastic material, such as polypropylene.

It is expedient if the intraocular lens storage position and the intraocular lens transfer position are in each case end positions of the transfer device. The intraocular lens storage position and the intraocular lens transfer position are different, in other words spatially spaced apart from one another. A stepless movement of the transfer device between the positions is preferably possible. It is advantageous if the movement of the transfer device is guided and a corresponding mounting is provided.

The injection device is preferably configured as an injector.

It is advantageous if the intraocular lens comprises an optical part and at least one haptic device, which is arranged on the optical part.

The intraocular lens is received or held in a safe, but releasable manner in the intraocular lens receiver. The intraocular lens is preferably held with a positive fit in the intraocular lens receiver, preferably by a plug connection, latching connection, snap-in connection or the like.

The at least one actuating means coupled to the transfer device for moving the transfer device between the intraocular lens storage position and the intraocular lens transfer position is preferably configured as a push button, slide element, pull element, release element for releasing a stored force, pivot element, latch element, electric switch element or the like.

The configuration in which at least one actuating means is provided on the transfer device, the actuating means being is arranged for the movement thereof between the intraocular lens storage position and the intraocular lens transfer position, for actuation by introducing the injection device into the storage container leads to a particularly simply configured transfer device that can be handled well. It is advantageous if the at least one actuating means is configured as an engagement element for interaction with the injection device when it is introduced into the storage container or as a lever arm. An actuating projection on the injection device preferably presses on the actuating means, so the transfer device is pivoted about a bearing axis into its intraocular lens transfer position.

In a preferred embodiment, the transfer device is pivotably mounted on the storage container. Corresponding bearing elements are preferably provided or arranged for this on the storage container. Alternatively, the transfer device is displaceably mounted on the storage container.

The at least one return spring means, which upon movement of the transfer device into the intraocular lens transfer position produces a transfer device return force to return the transfer device into the intraocular lens storage position, is preferably configured as a spring element or spring material block connected to the transfer device. It is advantageous if the spring element is a leaf spring element, a helical spring, a spiral spring, a torsion spring or the like. It is expedient if the leaf spring element is prestressed or is tensioned upon a bending. The spring material block is advantageously formed from a resilient material, which after loading automatically returns to its starting state again.

It is advantageous if the return spring means and the transfer device are connected to one another in one piece.

The injection device introduction stop for limiting the introduction movement of the injection device into the storage container is preferably arranged on the storage container or the transfer device. The injection device introduction stop preferably cooperates with a corresponding counter-stop on the injection device upon corresponding introduction of the injection device into the storage container. It is advantageous if the injection device introduction stop is formed by the intraocular lens itself or the intraocular lens receiver and the counter-stop is formed by an injection cartridge of the injection device.

The injection device can be introduced at least partially into the interior of the storage container through the injection device main introduction opening formed in the storage container for introducing the injection device.

The injection device through-opening for aligning a first guide wing of the injection device during introduction and the injection device positioning introduction opening for aligning a second guide wing of the injection device on introduction as well as the injection device positioning removal opening to align the second guide wing of the injection device on removal, said openings laterally adjoining the injection device main introduction opening, are arranged spaced apart from one another about the injection device main introduction opening and in each case extend laterally or radially away therefrom. It is advantageous if the guide wings are rigidly connected to an injection cartridge of the injection device.

The at least one pivoting link provided on the faces limiting the injection device positioning introduction opening and the injection device positioning removal opening forces a pivoting movement of the at least partially introduced injection device about the longitudinal axis thereof to transfer and receive the intraocular lens. A transfer of the intraocular lens is preferably only possible when the injection device is in its pivoted position. The at least one pivoting link preferably cooperates with a corresponding counter-face on the injection device on introduction.

It is advantageous if the storage container comprises a storage container base body and a separate closure device, the injection device main introduction opening being formed in the closure device.

The storage container thus has a storage container base body and a closure device, which is formed separately and can preferably also be removed again from the storage container base body. Alternatively, the storage container base body and the closure device are configured in one piece and non-separably with respect to one another.

The storage container base body and the closure device are advantageously rigidly connected to one another, preferably latched to one another.

By actuating the guide wings, which—on introduction of the injection device—pass through openings formed in the storage container, said openings laterally adjoining an injection device main introduction opening, wherein when the injection device is pivoted, one of the guide wings is preferably pivoted in relation to the other guide wing and can be removed again through a further opening in the storage container, the intraocular lens can be grasped and picked up by the injection cartridge.

The present invention will be explained in more detail below on the basis of drawings, which show exemplary embodiments only. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
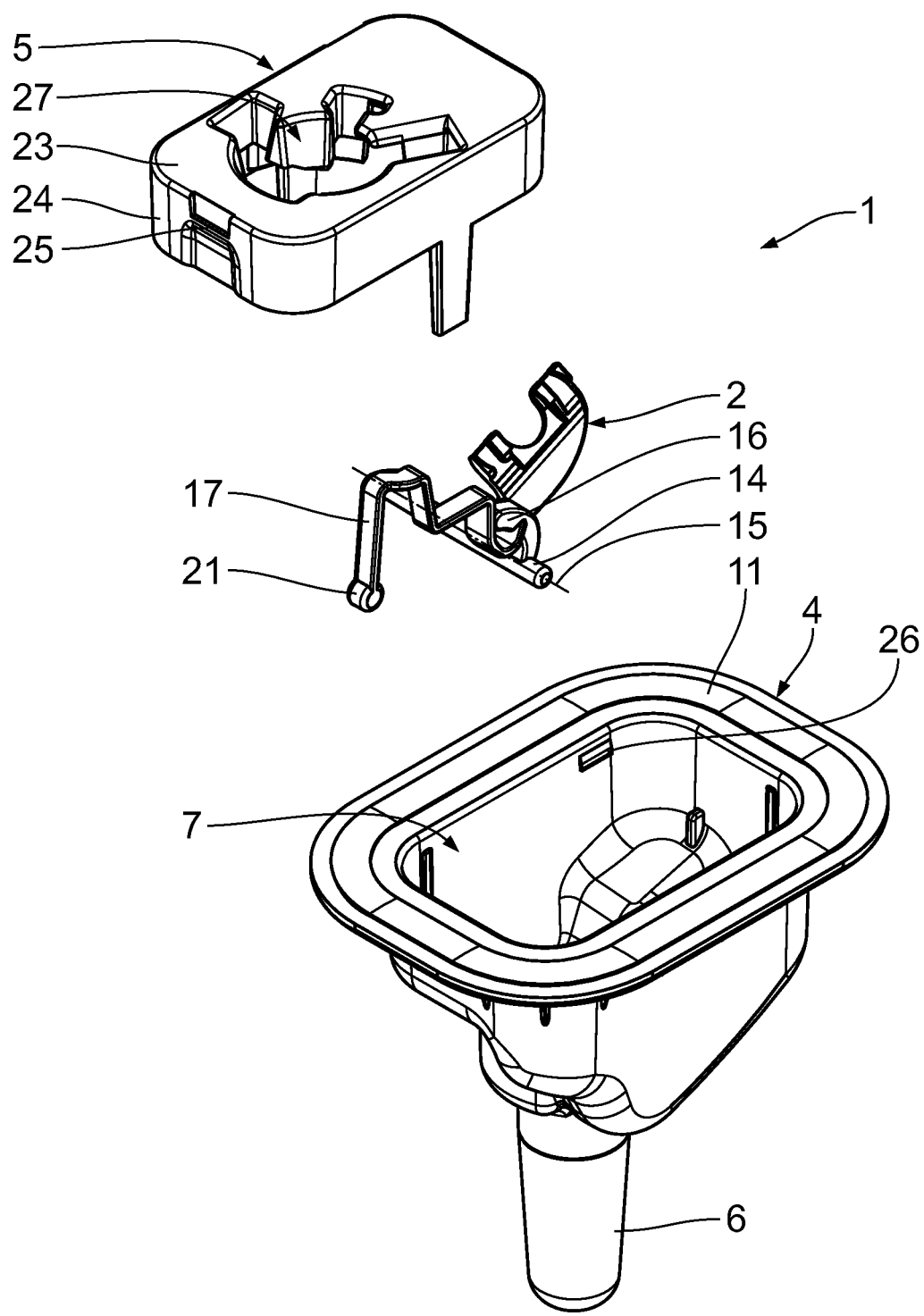
FIG. 1 is an exploded view of an intraocular lens storage system according to the invention.
Figure 2:
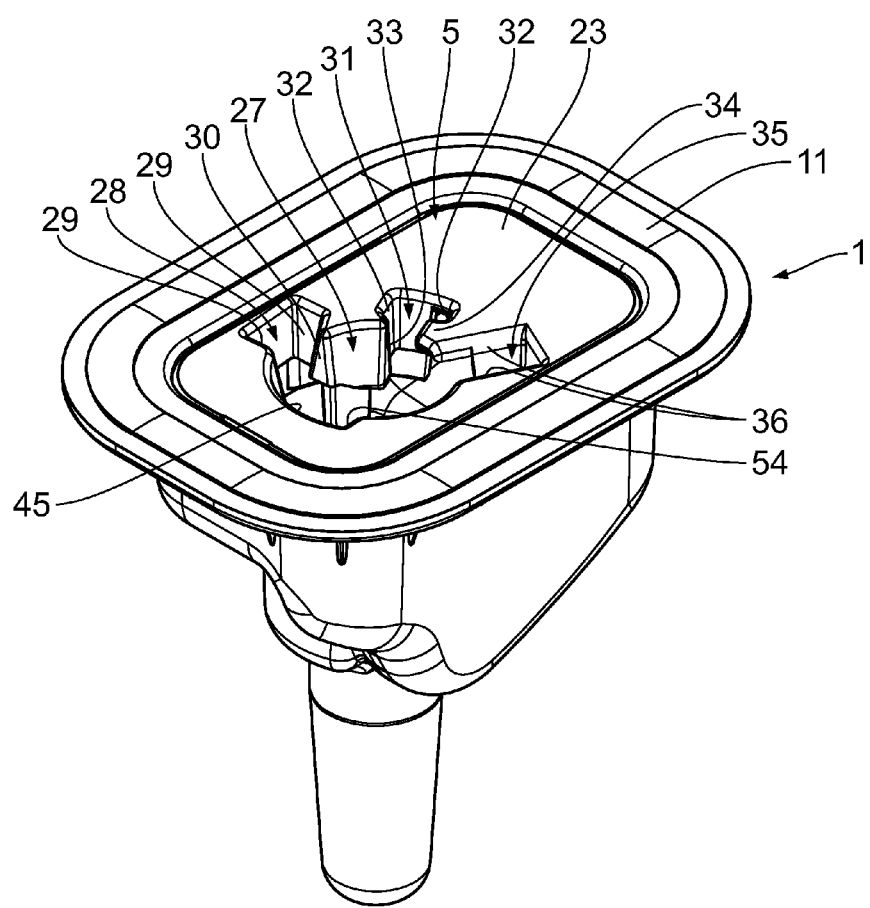
FIG. 2 is a view showing the intraocular lens storage system shown in FIG. 1 in the assembled state.
Figure 3:
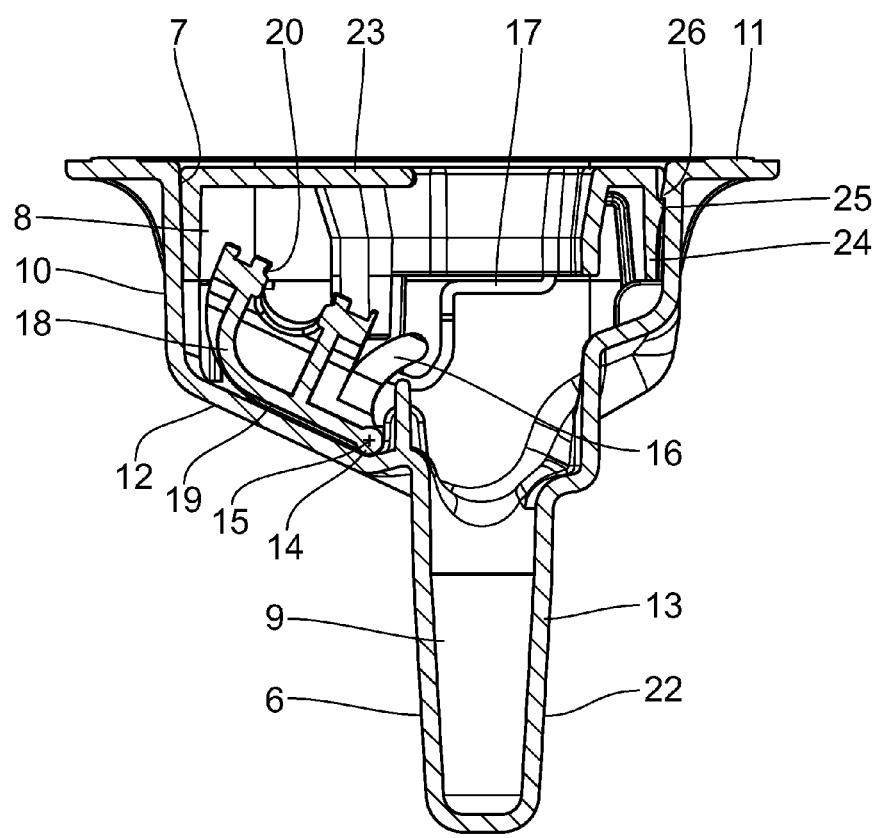
FIG. 3 is a longitudinal sectional view through the intraocular lens storage system shown in FIG. 2, in which its transfer device is in the intraocular lens storage position.
Figure 4:
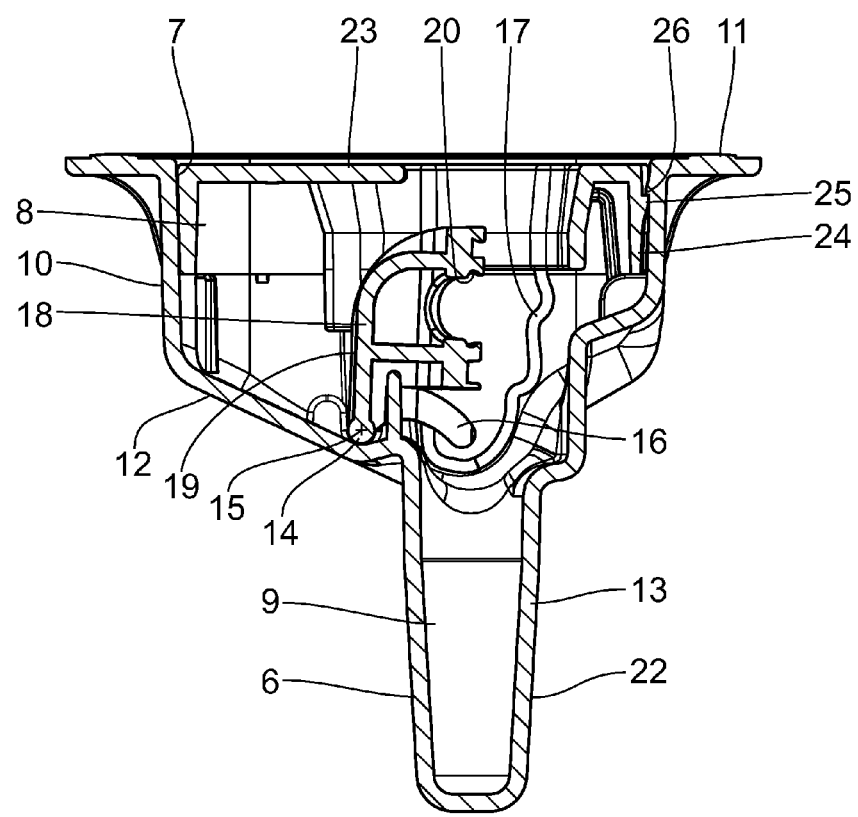
FIG. 4 is a longitudinal sectional view through the intraocular lens storage system shown in FIG. 2, in which its transfer device is in the intraocular lens transfer position.

An intraocular lens storage system comprises a storage container 1 and a transfer device 2, which is arranged in the storage container 1 and is movable between an intraocular lens storage position and an intraocular lens transfer position remote from the intraocular lens storage position by manual actuation. In the intraocular lens storage position, an intraocular lens (not shown) is stored in a safe and sterile manner in the storage container 1, while in the intraocular lens transfer position, a transfer of the intraocular lens to an injection device 3 is possible. An implantation of the intraocular lens into the eye of a patient is possible by means of the injection device 3.

The storage container 1 comprises a storage container base body 4 and a closure device 5, which, in the assembled state, are connected to one another rigidly but preferably so as to be releasable again.

The storage container base body 4 has an outer wall 6. The wall 6 limits a receiver opening 7, so the storage container base body 4 is outwardly open there. The storage container base body 4 has a first part portion 8, which adjoins the receiver opening 7 and is outwardly limited by the wall 6. A second part portion 9 of the storage container base body 4, which tapers in relation to the first part portion 8 and is outwardly limited by the wall 6, in turn adjoins the first part portion 8.

In the region of the first part portion 8, the storage container base body 4 is laterally outwardly limited by a side wall 10, which runs substantially perpendicular to an end flange-like side web 11. The side web 11 runs substantially in a plane. The receiver opening 7 is also located in this plane.

A main base 12, which is arranged opposite the receiver opening 7 and preferably runs obliquely with respect to the side wall 10 in regions, adjoins the side wall 10.

An indentation piece 13, which is closed at the end and is substantially configured in the manner of a tube, adjoins the main base 12. The indentation piece 13 extends perpendicular to the plane, in which the receiver opening 7 is located. The indentation piece 13 has a cross sectional area, which is smaller, preferably substantially smaller, than the area of the receiver opening 7. The indentation piece 13 is limited by an indentation web wall 22.

The transfer device 2 is in one piece. It has a bearing piece 14, which is elongate and cross sectionally substantially configured in the manner of a circular ring or circular. A coupling attachment 16, from which a return spring means 17 in turn emerges laterally, is rigidly connected to the bearing piece 14 on the peripheral side. The return spring means 17 emerges, spaced apart from the bearing piece 14, from the coupling attachment 16 and is originally repeatedly angled. It is elongate and strip-like.

Furthermore, an intraocular lens receiver body 18 is rigidly connected to the bearing piece 14 on the peripheral side. The intraocular lens receiver body 18 has a free contact face or edge 19, which preferably runs substantially tangentially with respect to the bearing piece 14. Opposite the contact face 19, the intraocular lens receiver body 18 has an intraocular lens receiver 20, which is arranged spaced apart from the contact face 19 in the perpendicular direction. When the intraocular lens receiver 20 is equipped, an intraocular lens (not shown) is held safely, but also so that it can be released again, in the intraocular lens receiver 20.

The bearing piece 14 is pivotably held in at least one bearing receiver (not shown), which is attached adjacent to the indentation piece 13 on the main base 12 and allows a pivoting of the transfer device 2 about a bearing axis 15. The transfer device 2 is mounted by means of the at least one bearing receiver on the storage container 1 or its main base 12. The transfer device 2 is rocker-like.

The return spring means 17 is supported here on the storage container 1, viewed more precisely in the first part portion 8, on the inside. It is advantageous if a region 21 of the return spring means 17 is spatially fixed on the storage container 1.

The wall 6 is formed by the side wall 10, the main base 12 and the indentation web wall 22.

In the assembled state of the intraocular lens storage system, the closure device 5 is inserted with a positive fit in the receiver opening 7. The closure device 5 is lid-like and has a lid portion 23, which is located approximately in the plane of the side web 11 in the inserted state of the closure device 5 and substantially closes the receiver opening 7. Furthermore, the closure device 5 has a side web 24, which runs approximately perpendicularly to the lid portion 23 and rests, at least in regions, on the side wall 10 on the inside. At least one first latching means 25, which, in the inserted state of the closure device 5, interacts with a corresponding counter-latching means 26 on the side wall 10 so as to latch, is arranged on the side web 24, on the outside.

An injection device main introduction opening 27, which is aligned according to the indentation piece 13 and completely penetrates the lid portion 23, is provided in the lid portion 23.

A positioning introduction opening 28, which completely penetrates the lid portion 23 and tapers from the outside in the direction of the main base 12 of the storage container base body 4, emerges laterally from the injection device main introduction opening 27. The positioning introduction opening 28 is thus laterally limited by two mutually opposing side walls 29, which are arranged on the lid portion 23 and converge from the outside in the direction of the main base 12.

Arranged between one of the side walls 29 and the injection device main introduction opening 27 is a web projection 30, which projects laterally into the injection device main introduction opening 27.

Furthermore, a positioning removal opening 31, which is arranged laterally spaced apart from the positioning introduction opening 28 in the lid portion 23 and completely penetrates the lid portion 23, laterally adjoins the injection device main introduction opening 27. The positioning removal opening 31 is again laterally limited by two mutually opposing side walls 32. The side walls 32 limiting the positioning removal opening 31 run substantially parallel to one another.

Between the side wall 32 adjacent to the positioning introduction opening 28 and the injection device main introduction opening 27, a web projection 33 is provided in the region of the injection device main introduction opening 27 on the lid portion 23, which reduces the through-connection between the positioning removal opening 31 and the injection device main introduction opening 27.

Furthermore, a blocking projection 34 projects from the lid portion 23 laterally from the side wall 32 remote from the positioning introduction opening 28 in the direction of the opposing side wall 32. The blocking projection 34 is flush with the lid portion 23 on the outside, but has a smaller thickness than the lid portion 23.

Moreover, a through-opening 35 laterally adjoins the injection device main introduction opening 27. The through-opening 35 is formed in the lid portion 23 and penetrates it completely. The positioning removal opening 31 is arranged between the though-opening 35 and the positioning introduction opening 28. The through-opening 35 is laterally limited by two mutually opposing side walls 36, which run parallel to one another.

Adjoining the injection device main introduction opening 27 laterally is furthermore a limiting opening 45, which is arranged adjacent to the positioning introduction opening 28 in the lid portion 23. The limiting opening 45 is arranged between the positioning introduction opening 28 and the through-opening 35.

The web projection 30 faces the limiting opening 45. The blocking projection 34 substantially springs away from the through-opening 35.

As already mentioned, the intraocular lens stored in the intraocular lens storage system can be implanted by the injection device 3 into the eye of a patient. The injection device 3 is configured as an injector and has an elongate tubular housing 37 and a longitudinal center axis 38.

The injection device 3 also has a holding or supporting projection 40 at a first end 39 of the housing 37, said supporting projection projecting radially in relation to the longitudinal center axis 38. Furthermore, the injection device 3 has a second end 41. A tapering body 42, which tapers on the outside and is hollow, is inserted into the housing 37 adjacent to the second end 41.

The injection device 3 also has a loading chamber 43, which is at least partially laterally open and is arranged adjacent to the second end 41. Furthermore, the injection device 3 comprises an injection cartridge 47, which is arranged in the loading chamber 43.

A longitudinally running guide web 44 is arranged opposite the opening of the loading chamber 43 laterally on the housing 37.

An actuating piston (not shown) is displaceably guided in the direction of the second end 41 in the housing 37. The actuating piston is rigidly connected to a piston rod (not shown), which axially passes through the housing 37 and projects outwardly in relation to the first end 39. The actuating piston can be actuated by the piston rod. An intraocular lens arranged in the loading chamber 43 or injection cartridge 47 can be guided through the tapering body 42 by displacing the actuating piston and can then be implanted in the eye of a patient.

The injection cartridge 47 is substantially formed by a tube piece 49, which extends in an introduction direction of the injection device 3. The tube piece 49 laterally outwardly limits an intraocular lens receiver space 50. It has a casing, which is separated or interrupted in the longitudinal direction of the tube piece 49, so the tube piece 49 can be folded open or folded together there. The tube piece 49 thus has, owing to the longitudinal interruption, two flap regions running longitudinally with free end edges 51 and 52. The end edges 51, 52 are arranged substantially adjacent to one another and are located substantially opposite one another. The tube piece 49 is cross sectionally substantially arc of a circle-shaped. The tube piece 49 is configured as a folding piece.

The injection cartridge 47 also has a first guide wing 53 and a second guide wing (not shown), which are substantially plate-like and extend laterally outwardly or in the radial direction with respect to the longitudinal center axis 38. A guide wing 53 is arranged on the tube piece 49 at each flap region. The connection regions of the guide wings 53 run parallel to the end edges 51, 52 and preferably also adjacent thereto.

The intraocular lens storage system and the injection device 3 together form an intraocular lens transfer arrangement.

The use of the intraocular lens transfer arrangement will be described in more detail below.

The closure device 5 is inserted in the receiver opening 7 and is fixed there latching on the storage container base body 4. The transfer device 2 is located in its original intraocular lens storage position. In this case, the contact face 19 rests on the main base 12 on the inside. An intraocular lens is received in the intraocular lens receiver 20.

Figure 5:
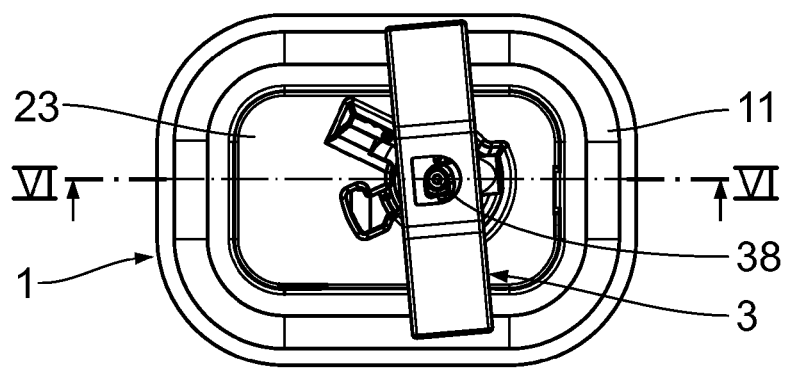
FIG. 5 is a plan view of an intraocular lens transfer arrangement with the intraocular lens storage system shown in FIG. 2, in which the injection device is in a starting position.
Figure 6:
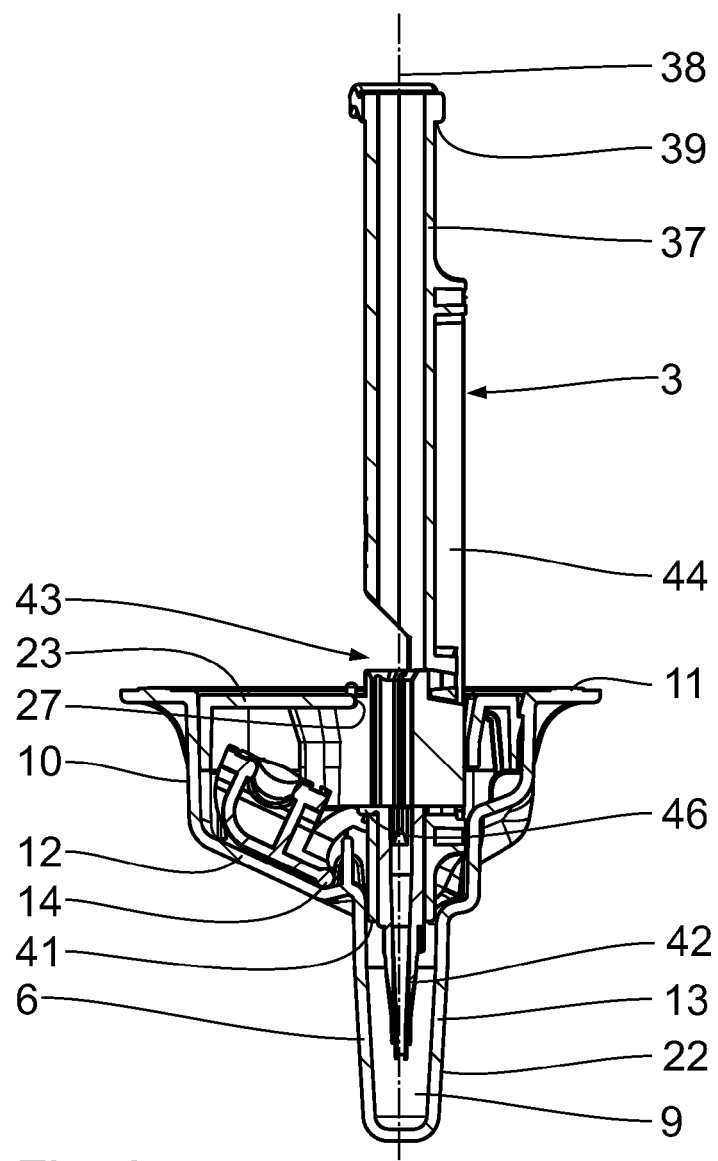
FIG. 6 is a longitudinal sectional view through the intraocular lens transfer arrangement shown in FIG. 5 along the section line VI-VI in FIG. 5.
Figure 7:
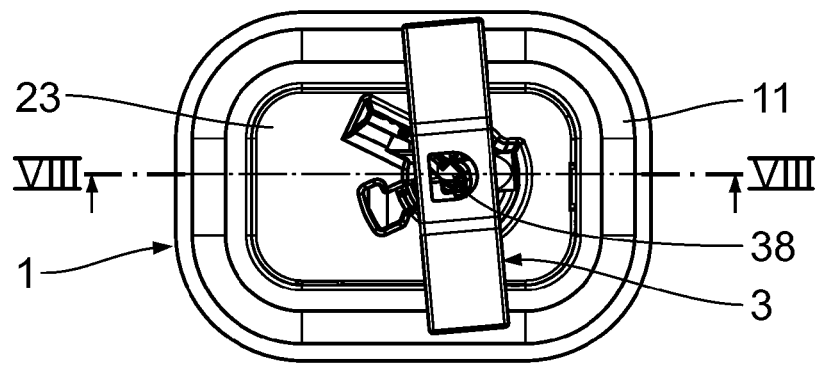
FIG. 7 is a plan view according to FIG. 5, in which the injection device is in an introduction position.
Figure 8:
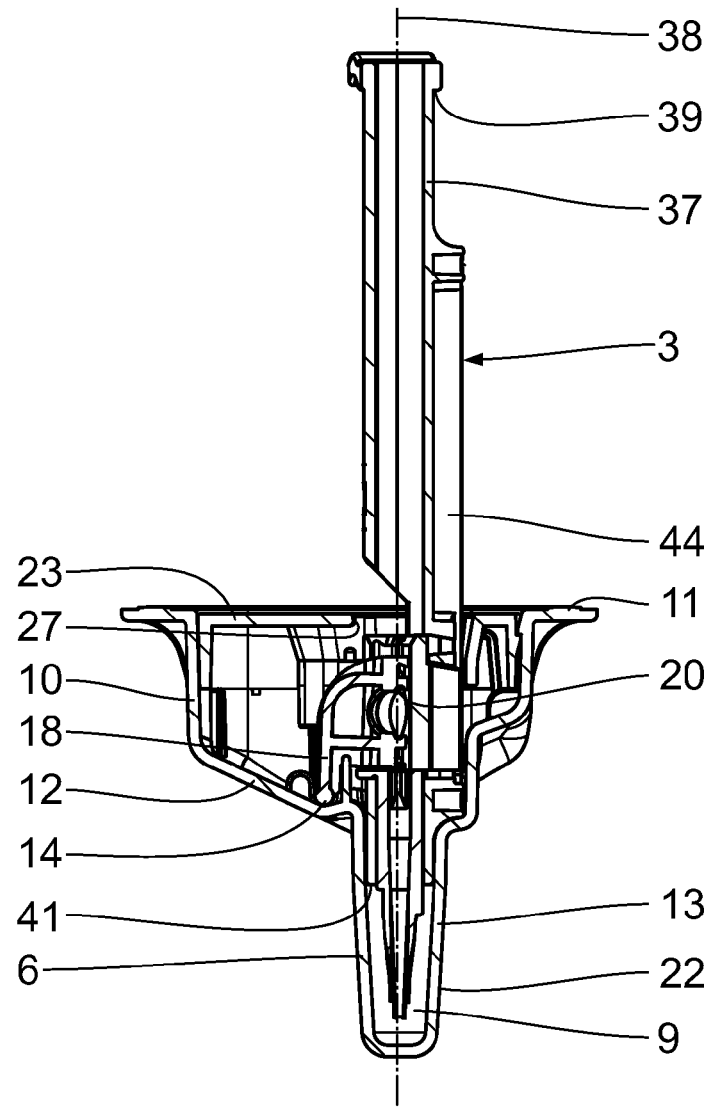
FIG. 8 is a longitudinal sectional view through the intraocular lens transfer arrangement shown in FIG. 7 along the section line VIII-VIII in FIG. 7.

According to FIG. 5, 6, the injection device 3 is already partially introduced into the storage container 1. In this case, the injection device 3 with its main body penetrates the injection device main introduction opening 27 and projects with its tapering body 42 into the indentation piece 13. The injection cartridge 47 is located here in the first part portion 8 of the storage container 1. The injection device 3 is in its starting position. The intraocular lens transfer arrangement can thus be provided pre-adjusted or preassembled in this state or created by corresponding introduction of the injection device 3. The guide web 44 passes through the limiting opening 45. An actuating projection 46 arranged on the injection device 3 and, projecting laterally therefrom, rests on the coupling attachment 16 at the top.

The injection device 3 is then introduced further into the storage container 1 along the longitudinal center axis 38 in an introduction direction by applying a corresponding introduction force. In this case, the actuating projection 46 presses on the coupling attachment 16, so the transfer device 2 is pivoted about the bearing axis 15 into its intraocular lens transfer position. The contact face 19 is lifted from the main base 12. The bearing axis 15 runs perpendicular to the introduction direction. The coupling attachment 16 thus forms an actuating means for actuating the transfer device 2. In this case, the transfer device 2 is pivoted through about 15° to 90°, preferably through about 40° to 75°. In the intraocular lens transfer position, the intraocular lens receiver 20 is in the injection cartridge 47 or adjacent thereto. Viewed more precisely, the intraocular lens in the intraocular lens transfer position is located in the transfer device 2 directly in front of the intraocular lens receiver space 50. The elongate return spring means 17 is bent and tensioned by the pivoting movement of the transfer device 2. It thus produces a return force. A further axial introduction of the injection device 3 is prevented by a stop of the intraocular lens on the tube piece 49. The first guide wing 53 passes through the through-opening 35 here. It is arranged between the two side walls 36 here, which prevent a pivoting of the injection cartridge 47 about the longitudinal center axis 38 by a stop on the first guide wing 53.

The second guide wing passes through the positioning introduction opening 28 here. The two guide wings 53, for passing through the openings 28, 35, are to be correspondingly folded open or pivoted apart by bending open the tube piece 49, so an introduction of the guide wings 53 through the openings 28, 35 is possible.

Figure 9:
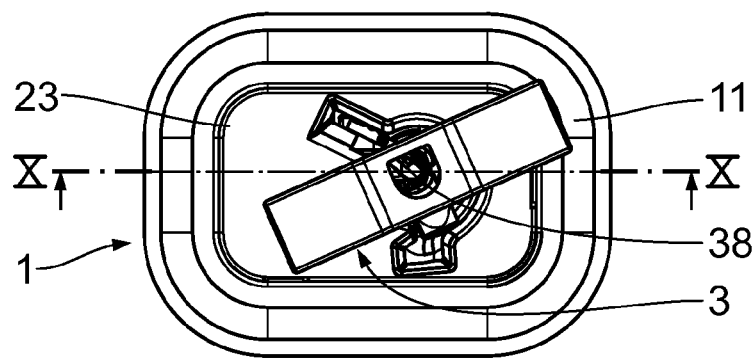
FIG. 9 is a plan view according to FIG. 5, the injection device being in a transfer position.
Figure 10:
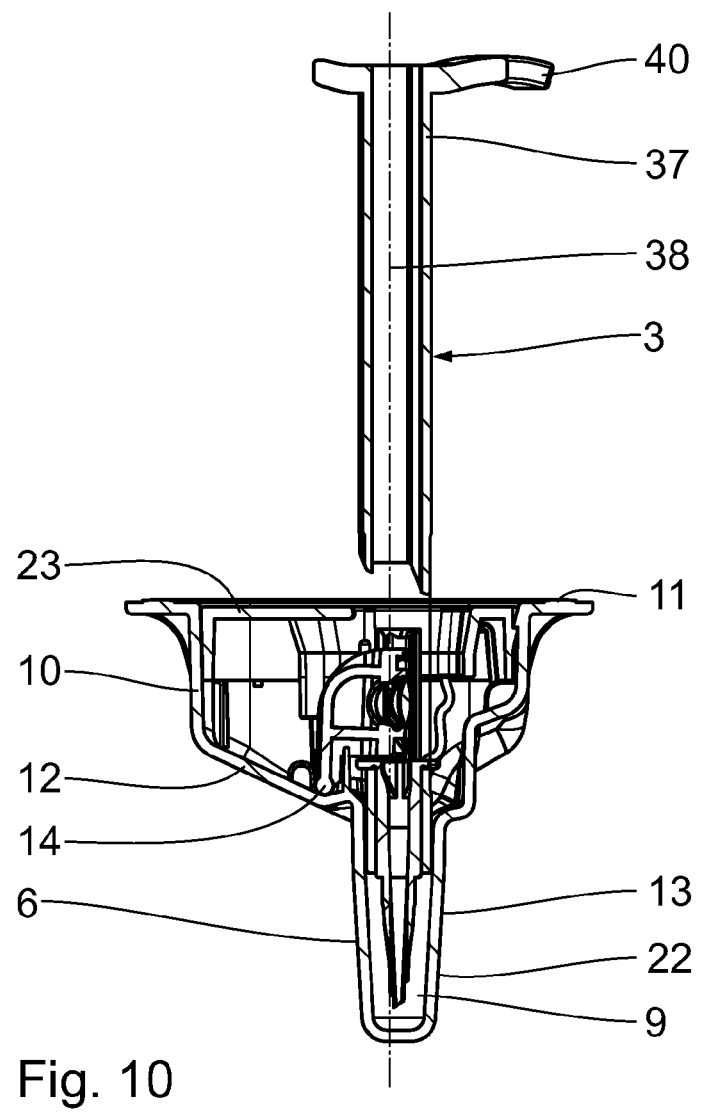
FIG. 10 is a longitudinal sectional view through the intraocular lens transfer arrangement shown in FIG. 9 along the section line X-X in FIG. 9.

Referring to FIGS. 9 and 10, the injection device 3 is then manually pivoted about the longitudinal center axis 38 relative to the storage container 1. In this case, the intraocular lens receiver 20 completely rotates laterally into the injection cartridge 47 of the injection device 3. In the process, the intraocular lens is forced out of the intraocular lens receiver 20, more preferably pressed, and transferred to the injection device 3 or its injection cartridge 47. By means of the rotation of the injection device 3 about the longitudinal center axis 38, the end edges 51, 52 are moved further toward one another, so the intraocular lens receiver space 50 is further closed. In the process, the flap regions encompass the intraocular lens. This pivoting movement is predetermined by the side walls 29 of the positioning introduction opening 28 and the side walls 32 of the positioning removal opening 31, which form pivoting links. Contact of the guide web 44 with the web projection 30 prevents pivoting that is too far in this direction. Pivoting in the opposite direction is prevented by contact of a contact face 54 with the web projection 30. The contact face 54 laterally limits the limiting opening 45. It is provided at the end of the limiting opening 45 remote from the positioning introduction opening 28. The guide web 44 then rests on the web projection 30, so a further pivoting of the injection device 3 relative to the storage container 1 is prevented. The web projection 30 thus forms a pivot stop.

Upon a return movement of the transfer device 2 into the intraocular lens storage position, the intraocular lens is released by the flap regions from the transfer device 2 and transferred into the intraocular lens receiver space 50.

On conclusion of the pivoting movement, the second guide wing introduced through the positioning introduction opening 28 is in a second, pivoted position, so it is aligned according to the positioning removal opening 31.

Figure 11:
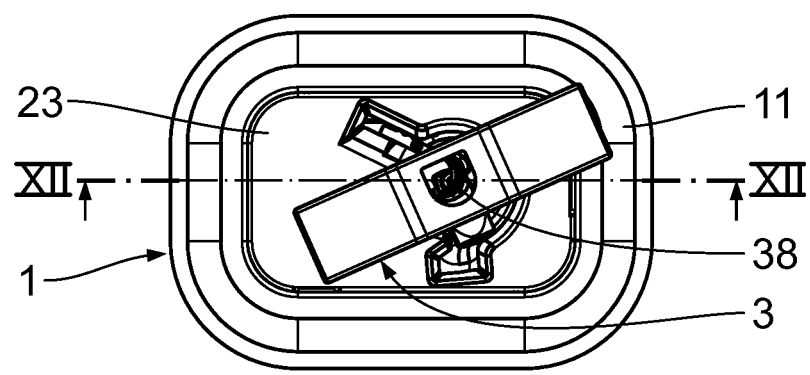
FIG. 11 is a plan view according to FIG. 5, in which the injection device is in an extraction position.
Figure 12:
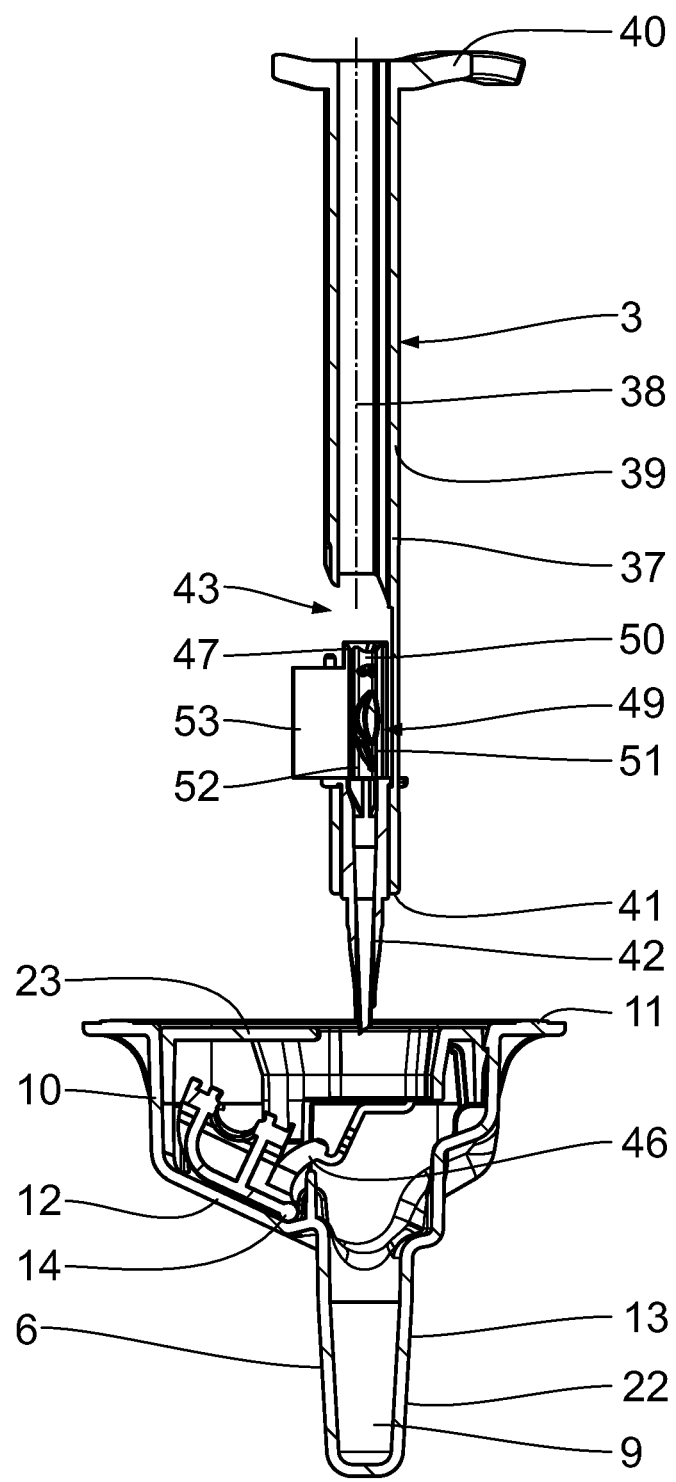
FIG. 12 is a longitudinal sectional view through the intraocular lens transfer arrangement shown in FIG. 11 along the section line XII-XII in FIG. 11.

The injection device 3 is then removed again from the storage container 1 counter to the introduction direction (FIGS. 11, 12). The intraocular lens is now located in the injection device 3. The transfer device 2 is pivoted back again into its intraocular lens storage position about the bearing axis 15 by the return spring means 17. The second guide wing in this case passes through the positioning removal opening 31. The first guide wing 53 again passes through the through-opening 35.

The intraocular lens can now be implanted into the eye of a patient using the injection device 3.

While specific embodiments of the invention have been shown and described in detail to illustrate the application of the principles of the invention, it will be understood that the invention may be embodied otherwise without departing from such principles.

The invention claimed is:

1. An intraocular lens storage system for storing an intraocular lens, comprising:
   a storage container for storing the intraocular lens; and
   an actuable transfer device, which is arranged in the storage container, with an intraocular lens receiver for receiving the intraocular lens, wherein the transfer device is movable between an intraocular lens storage position for storing the intraocular lens in the storage container, and an intraocular lens transfer position for transferring the intraocular lens to an injection device, wherein an injection device main introduction opening for introducing the injection device into the storage container is formed in the storage container, wherein an injection device through-opening for aligning a first guide wing of the injection device during introduction and an injection device positioning introduction opening for aligning a second guide wing of the injection device on introduction as well as an injection device positioning removal opening to align the second guide wing of the injection device on removal laterally adjoin the injection device main introduction opening.

2. The intraocular lens storage system according to claim 1, wherein at least one actuating means coupled to the transfer device for moving the transfer device between the intraocular lens storage position and the intraocular lens transfer position is provided on the storage container.

3. The intraocular lens storage system according to claim 1, wherein provided on the transfer device is at least one actuating means, which is arranged for the movement thereof between the intraocular lens storage position and the intraocular lens transfer position, for actuation by introducing the injection device into the storage container.

4. The intraocular lens storage system according to claim 1, wherein the transfer device is pivotably mounted on the storage container.

5. The intraocular lens storage system according to claim 1, wherein at least one return spring means, which upon movement of the transfer device into the intraocular lens transfer position produces a transfer device return force to return the transfer device into the intraocular lens storage position, is connected to the transfer device.

6. The intraocular lens storage system according to claim 1, further comprising:
   an injection device introduction stop for limiting the introduction movement of the injection device into the storage container.

7. The intraocular lens storage system according to claim 1, wherein faces limiting the injection device positioning introduction opening and the injection device positioning removal opening have at least one pivoting link for forcing a pivoting movement of the at least partially introduced injection device about the longitudinal center axis thereof relative to the storage container to transfer the intraocular lens.

8. The intraocular lens storage system according to claim 7, wherein the at least one pivoting link has a pivoting link face on the storage container, said pivoting link face extending in at least one of an oblique direction and a transverse direction to an introduction direction of the injection device into the storage container.

9. The intraocular lens storage system according to claim 7, wherein a pivot stop on the storage container limits a maximum pivoting movement of the injection device relative to the storage container.

10. An intraocular lens transfer arrangement comprising:
    an intraocular lens storage system, said intraocular lens storage system comprising a storage container for storing an intraocular lens and an actuable transfer device, which is arranged in the storage container, with an intraocular lens receiver for receiving the intraocular lens, wherein the transfer device is movable between an intraocular lens storage position for storing the intraocular lens in the storage container, and an intraocular lens transfer position for transferring the intraocular lens to an injection device; and
    an injection device for introduction into the storage container of the intraocular lens storage system, wherein the transfer device in the intraocular lens transfer position transfers the intraocular lens to the injection device for implantation, the injection device comprising an injection cartridge, the injection cartridge being formed by a folding piece with two free folding regions, which are movable in relation to one another and in each case carry a guide wing extending laterally outwardly, the guide wings, on introduction of the injection device, passing through openings formed in the storage container, said openings laterally adjoining an injection device main introduction opening.

11. The intraocular lens transfer arrangement according to claim 10, wherein when the injection device is pivoted, one of the guide wings is pivoted in relation to the other guide wing and can be removed again through a further opening in the storage container.

12. A method for transferring an intraocular lens to an injection device, the method comprising:
    providing an intraocular lens storage system, said intraocular lens storage system comprising a storage container for storing an intraocular lens and an actuable transfer device, which is arranged in the storage container, with an intraocular lens receiver for receiving the intraocular lens, wherein the transfer device is movable between an intraocular lens storage position for storing the intraocular lens in the storage container, and an intraocular lens transfer position for transferring the intraocular lens to an injection device, wherein an injection device main introduction opening for introducing the injection device into the storage container is formed in the storage container, wherein an injection device through-opening for aligning a first guide wing of the injection device during introduction and an injection device positioning introduction opening for aligning a second guide wing of the injection device on introduction as well as an injection device positioning removal opening to align the second guide wing of the injection device on removal laterally adjoin the injection device main introduction opening; and actuating the transfer device to move the transfer device from the intraocular lens storage position into the intraocular lens transfer position to transfer the intraocular lens to the injection device.

\* \* \* \* \*